(12) United States Patent
Gulbins

(10) Patent No.: US 7,812,015 B2
(45) Date of Patent: Oct. 12, 2010

(54) PROPHYLAXIS AND TREATMENT OF INFECTIOUS DISEASES

(75) Inventor: Erich Gulbins, c/o Institut für Molekularbiologie, Universität Essen, Hufelandstrasse 55, 45122 Essen (DE)

(73) Assignees: Erich Gülbins, Essen (DE); Claus Adams, Wittmund (DE)

( * ) Notice: Subject to any disclaimer, the term of this patent is extended or adjusted under 35 U.S.C. 154(b) by 631 days.

(21) Appl. No.: 10/524,815

(22) PCT Filed: Aug. 21, 2003

(86) PCT No.: PCT/EP03/09254

§ 371 (c)(1),
(2), (4) Date: Feb. 18, 2005

(87) PCT Pub. No.: WO2004/017949

PCT Pub. Date: Mar. 4, 2004

(65) Prior Publication Data

US 2005/0209219 A1   Sep. 22, 2005

(30) Foreign Application Priority Data

Aug. 23, 2002  (DE) ................. 102 39 531

(51) Int. Cl.
*A01N 43/00* (2006.01)
*A01N 43/46* (2006.01)
*A01N 43/62* (2006.01)
*A61K 31/55* (2006.01)

(52) U.S. Cl. ............... 514/217; 514/213.01; 514/220

(58) Field of Classification Search ........... 514/217, 514/213.01, 220; 424/130.1
See application file for complete search history.

(56) References Cited

U.S. PATENT DOCUMENTS

| 5,233,024 | A |   | 8/1993  | Schreiber et al. |
| 5,244,881 | A |   | 9/1993  | Coutel-Egros |
| 5,373,005 | A |   | 12/1994 | McCann et al. |
| 5,569,677 | A | * | 10/1996 | Daines .................. 514/570 |
| 6,248,528 | B1 | * | 6/2001 | Chen et al. ............... 435/6 |
| 6,608,101 | B1 | * | 8/2003 | Sikorski et al. ......... 514/443 |
| 2002/0177126 | A1 |   | 11/2002 | Young et al. |
| 2005/0054588 | A1 |   | 3/2005 | Borody |

FOREIGN PATENT DOCUMENTS

| WO | 90/14089 A1 | 11/1990 |
| WO | 99/41373 | 8/1999 |
| WO | 00/33885 | 6/2000 |
| WO | 00/56890 | 9/2000 |

OTHER PUBLICATIONS

Haimovitz-Friedman, A. et al. "Lipopolysaccharide induces disseminated endothelial apoptosis requiring ceramide generation," (1997). J. Exp. Med., 186 (11):1831-1841.*
Webster Ninth New Collegiate Dictionary. 2000. Definition of Prevent. p. 1.*
Nature Medicine, Mar. 2003, vol. 9, No. 3, pp. 322-330.*
Bilgi et al. Canadian Family Physician. May 1979; vol. 25, pp. 619-620, 622, 624-625.*
New York Times. Dec. 1997, Inhalant Drug Approved for Cystic Fibrosis, pp. 1-3.*
Sanders et al. Am J. Respir. Crit. Care Med., 2000, vol. 162, pp. 1905-1911.*
Baillie, R. The Lancet, 1967, pp. 369-370.*
Albouz, S., et al., "Effect of Tricyclic Antidepressants on Sphingomyelinase and Other Sphingolipid Hydrolases in C6 Cultured Glioma Cells", *Neuroscience Letters*, vol. 36, No. 3, pp. 311-315, (1983). XP008023932.
Baumann, N., et al., "Effect of Tricyclic Antidepressants on Lysosomal Sphingomyelinase Activity", *NATO ASI Series, Series A: Life Sciences*, vol. 150 (Lipid Storage Disord.), pp. 627-634, (1988). XP008023933.
Brown, D.A., et al., "Functions of Lipid Rafts in Biological Membranes", *Annu. Rev. Cell Dev. Biol.*, vol. 14, pp. 111-136, (1998).
Clapham, P.R., et al., "HIV-1 Receptors and Cell Tropism", *British Medical Bulletin*, vol. 58, pp. 43-59, (2001).
Claus, S.R., et al., "Modulation of the Ceramide Level, A Novel Therapeutic Concept?", *Current Drug Targets*, vol. 1, No. 2, pp. 185-205, (2000).
Dutta, P., et al., "Antimalarial Properties of Imipramine and Amitriptyline", *J. Protozool.*, vol. 37, No. 1, pp. 54-58, (1990).
Grassmé, H., et al., "Acidic Spingomyelinase Mediates Entry of N. Gonorrhoeae Into Nonphagocytic Cells", *Cell*, vol. 91, pp. 605-615, (1997).

(Continued)

*Primary Examiner*—Sreeni Padmanabhan
*Assistant Examiner*—Samira Jean-Louis
(74) *Attorney, Agent, or Firm*—Karl Bozicevic; Bozicevic, Field & Francis LLP

(57) ABSTRACT

The invention relates to the use of inhibitors of acid sphingomyelinase and/or of inhibitors of products of the reaction catalyzed by this enzyme, for the prophylaxis and/or treatment of infectious diseases and/or diseases which are influenced by infections during the course thereof. The cited products especially include ceramide. Preferably neutralizing antibodies and/or antidepressants, especially tricyclic and/or tetracyclic antidepressants, are used as inhibitors.

6 Claims, 6 Drawing Sheets

OTHER PUBLICATIONS

Grassmé, H., et al., "CD95 Signaling Via Ceramide-Rich Membrane Rafts", *The Journal of Biological Chemistry*, vol. 276, No. 23, pp. 20589-20596, (2001).

Grassmé, H., et al., "Ceramide-Rich Membrane Rafts Mediate CD40 Clustering", *The Journal of Immunology*, pp. 298-307, (2001).

Harder, T., et al., "Caveolae, DIGs, and the Dynamics of Sphingolipid-Cholesterol Microdomains", *Current Opinion in Cell Biology*, vol. 9, pp. 534-542, (1997).

Hauck, C.R., et al., "Acid Sphingomyelinase is Involved in CEACAM Receptor-Mediated Phagocytosis of *Neisseria gonorrhoeae*", *FEBS Letters*, vol. 478, pp. 260-266, (2000).

Kristiansen, J.E., et al., "Inhibition of HIV Replication by Neuroleptic Agents and Their Potential Use in HIV Infected Patients With AIDS Related Dementia", *International Journal of Antimicrobial Agents*, vol. 14, pp. 209-213, (2000). XP001056998.

Lauer, S.A., et al., "Sphingolipid Synthesis as a Target for Chemotherapy Against Malaria Parasites", *Proc. Natl. Acad. Sci. USA*, vol. 92, pp. 9181-9185, (1995).

Munoz-Bellido, J.L., et al., "Antimicrobial Activity of Psychotropic Drugs Selective Serotonin Reuptake Inhibitors", *International Journal of Antimicrobial Agents*, vol. 14, pp. 177-180, (2000).

Popik, W., et al., "Human Immunodeficiency Virus Type 1 Uses Lipid Raft-Colocalized CD4 and Chemokine Receptors for Productive Entry Into CD4+ T Cells", *Journal of Virology* vol. 76, No. 10, pp. 4709-4722, (2002).

W. Linli, "Clinical Application and Adverse Reaction of Nystatin". *China Pharmacaceuticals*, vol. 10:1, pp. 58-59, 2001.

Prince et al., "KGF alters gene expression in human airway epithelia: potential regulation of the inflammatory response." *Physiol. Genomics*, v. 6, pp. 87-89, 2001.

Shute et al., "Growth Factors in cystic fibrosis—when is not enough." *Paediatric Respiratory Reviews*, v. 4, pp. 120-127, 2003.

Alfsen et al., "Secretory IgA Specific for a Conserved Epitope on gp41 Envelope Glycoprotein Inhibits Epithelial Transcytosis of HIV-1" Journal of Immunology (2001) 166:6257-6265.

Corda et al., "Rapid Reactive Oxygen Species Production by Mitochondria in Endothelial Cells Exposed to Tumor Necrosis Factor-alpha is Mediated by Ceramide" Am. J. Respir. Cell Mol. Biol. (2001) 24:763-768.

Gajate et al., "The antitumor ether lipid ET-18-OCH3 induces apoptosis through translocation and capping of Fas/CD95 into membrane rafts in human leukemic cells" Blood (2001) 98:3860-3883.

Rousson et al., "Preparation of an anti-acid sphingomyelinase monoclonal antibody for the quantitative determination and polypeptide analysis of lysosomal sphingomyelinase in fibroblasts from normal and Niemann-Pick type A patients" J. Immunol. Methods (1993) 160:199-206.

Triantafilou et al., "Mediators of innate immune recognition of bacteria concentrate in lipid rafts and facilitate lipopolysaccharide-induced cell activation" Journal of Cell Science (2002) 115:2603-2611.

Vielhaber et al. "Mouse anti-ceramide antiserum: a specific tool for the detection of endogenous ceramide" Glycobiology (2001) 11(6):451-457.

Asay, "Cyctic Fibrosis" California Medicine, 102:292-300 (1965).

Corda et al., "Rapid Reactive Oxygen Species Production by Mitochondria in Endothelial Cells Exposed to Tumor Necrosis Factor-alpha is Mediated by Ceramide" Am J Respir Cell Mol Biol, 24(6):762-8 (2001).

Hurwitz et al., "The Tricyclic Antidepressant Desipramine Causes Proteolytic Degradation of Lysosomal Sphingomyelinase in Human Fibroblasts" biol Chem Hoppe Seyler, 375(7):447-50 (1994).

* cited by examiner

PROPHYLAXIS AND TREATMENT OF INFECTIOUS DISEASES

The present invention relates to the use of active ingredients which are suitable for the prophylaxis and/or treatment of infectious diseases.

Since infectious diseases continue to represent a great medical problem around the world, studies on the therapy and the prophylaxis of such diseases have long been the subject of intensive research. For example, immense costs are continually expended in order to develop novel antibiotics. These antibiotics are necessary in order to be able to control bacteria, fungi, protozoa or parasites as pathogens of infectious diseases. It is particularly necessary in this connection to take account of the increasing problem of the continuous new development of pathogen resistances.

The therapy of infectious diseases caused by viruses or prions represents a particular difficulty. Because these pathogens lack their own metabolism, they cannot be attacked by antibiotics so that, in general, only symptomatic therapy is possible.

In order to improve the prophylaxis and treatment of infectious diseases and, in particular, to take account of the problems mentioned, the object of the invention is to provide active ingredients which are particularly suitable for the prophylaxis and treatment of infectious diseases.

The object is achieved by a use of inhibitors as is described in the original claims. The wording of all the claims is hereby included in this description by reference.

Inhibitors of acid sphingomyelinase and/or inhibitors of products resulting from the reaction catalyzed by acid sphingomyelinase are used according to the invention for the prophylaxis and/or treatment of infectious diseases. These products include in particular ceramide, which results from the cleavage of sphingolipids. Experiments which led to this novel use of inhibitors of this type showed that effective prevention of infection of eukaryotic cells with various pathogenic organisms, for example bacteria, viruses, fungi and parasites, is possible therewith. Besides the prophylaxis and/or treatment of infectious diseases, said inhibitors can also be advantageously employed for the prophylaxis and/or treatment of diseases whose clinical course is at least partly determined by infections. One example of such diseases is cystic fibrosis.

These surprising results are based on the fact that ceramide-rich membrane platforms in the plasma membrane of eukaryotic cells are necessary for infection of eukaryotic cells with pathogens. These relatively large platforms in the plasma membrane of eukaryotic cells are formed by fusion of very small distinct domains in the plasma membrane, called rafts. These rafts consist of cholesterol and sphingolipids, especially sphingomyelin, which are very firmly associated together, thus separating the phospholipids of the plasma membrane and forming these small distinct domains. The sphingolipid occurring most commonly in rafts is sphingomyelin, which consists of the very hydrophobic ceramide residue and the hydrophilic phosphorylcholine head group. Ceramide is an amide ester from the sphingoid base D-erythro-sphingosine and a fatty acid, normally with a chain length from $C_{16}$ to $C_{26}$. Hydrogen bonds hydrophobic van der Waal interactions between the cholesterol ring system and sphingolipids and between the head groups of the sphingolipids lead to lateral association of the sphingolipids and the cholesterol in the plasma membrane and a spontaneous separation from the other phospholipids (Brown D. A., London E. (1998). Functions of lipid rafts in biological membranes. Annu. Rev. Cell. Dev. Biol. 14: 111-367; Harder T., Simons K. (1997). Caveolae, DIGs, and the dynamics of sphingolipid cholesterol microdomains. Curr. Opin. Cell. Bioil. 9: 534-542). This results in the very small, distinct sphingolipid- and cholesterol-rich membrane domains which are referred to as rafts. The structure and function of rafts is destroyed by extracting the cholesterol, which probably acts as spacer between the sphingolipids with their relatively large head groups, from the rafts.

A mechanism which mediates the formation of membrane platforms from rafts, the clustering or aggregation of recepts in these membrane platforms and the infection of cells with pathogenic bacteria and viruses has been idenetified according to the invention. For example, stimulation via CD95 of the CD40 receptor, infection with *Pseudomonas aeruginosa, Staphylococcus aureus, Neisseriae gonorhoeae* or else infection of human cells with rhinovirus is followed by release of ceramide from sphingomyelin in rafts. The formation of ceramide in rafts leads, owing to the biophysical properties of ceramide, to fusion of small rafts to give large, ceramide-rich platforms in the plasma membrane.

Results which led to the invention show that these small rafts are fused to the larger platforms mentioned by the enzyme acid sphingomyelinase and by the ceramide which is released by the reaction catalyzed by this enzyme.

The physiological significance of these platforms has recently been described by Grassme et al. (J. Biol. Chem. 276, 20589-20596 (2001); J. Immunol. 168, 298-307 (2002)). The authors were able to show that the ceramide-rich platforms serve to relay signals from the extracellular space into the interior of the cell. This entails initial induction, through activation of various receptors, e.g. CD95 and CD40, of a translocation of the enzyme acid sphingomyelinase to the outside of the membrane. There, ceramide is liberated from sphingomyelin by the acid sphingomyelinase and spontaneously aggregates into rafts. This results in the transformation of rafts into very hydrophobic membrane regions. These ceramide aggregates also show the tendency to fuse spontaneously to give larger membrane platforms. Activated receptors such as CD95 and CD40 aggregate in these ceramide-rich membrane platforms, as is necessary for relaying a signal via these receptors into the cell.

It has now been possible to show, interestingly, within the framework of the invention that these platforms additionally make it possible for pathogenic organisms to penetrate in via these corresponding membrane sections. The enzyme acid sphingomyelinase is crucially involved in the formation of these "portals of entry" for pathogenic organisms into the eukaryotic cell, because the ceramides which form the membrane platforms are products of the reaction catalyzed by this enzyme. This process is initiated by the pathogens causing, by a mechanism which is as yet unknown, the acid sphingomyelinase to be transported in intracellular vesicles to the cell surface or into the outer side of the membrane. The enzyme brings about the degradation of sphingomyelin to ceramide in the membrane there. The inventors have been able to show this importance of ceramide-rich membrane platforms for infections with pathogenic bacteria and viruses in particles for the example of infection of mammalian cells with Pseudomonas aeruginosa. Infection of mammalian cells with *P. aeruginosa* activates acid sphingomyelinase and thus induces the liberation of ceramide.

A further task of the enzyme acid sphingomyelinase has also been described in connection with the invasion of gonococci into eukaryotic cells by Grassme et al. (Cell, Vol. 91, 605-615, 1997). The authors were able to show that acid sphingomyelinase is involved in a signal transduction chain in the host cell which mediates the invasion of a particular gonococcal strain. Certain surface proteins on the bacterial pathogen, called Opa proteins, are crucial in this connection. They bind to a specific receptor of the eukaryotic host cell, so that a phospholipase C is activated and diacylglycerol is formed. This diacylglycerol in turn activates acid sphingomyelinase, so that ceramide is formed by the reaction catalyzed by this enzyme. This signal cascade was, however, inducible only by very particular bacteria or strains. In particular, the inducibility of this signal cascade depended on the Opa proteins on the bacterium. This mechanism is therefore completely different and very specific when compared with the general mechanism of invasion and infection via said membrane platforms which has been discovered in connection with the invention.

The prevention according to the invention of the formation of the membrane platforms and/or the destruction of previously formed membrane platforms prevents the pathogens penetrating into the host cell. This is achieved within the framework of the invention preferably through the use of inhibitors of acid sphingomyelinase and/or of inhibitors of the products of the reaction catalyzed by this enzyme. This has the advantage compared with conventional methods for the therapy of infectious diseases that the target for the active ingredient is situated on the host cell, that is the eukaryotic cell to be infected. The invention makes available a general inhibitor of infection which can be employed for a large number of quite different pathogens (e.g. bacteria, viruses, parasites, protozoa or fungi). This is a crucial advantage compared with, for example, the use of antibiotics, each of which must be directed very specifically against the pathogen to be controlled. The use according to the invention now also makes it possible to take measures against viral infections in a way not previously possible in general. In addition, the use according to the invention avoids the problem of the pathogens developing resistances, because the active ingredient is directed not against the pathogens but against the reactions induced in the host cell by this pathogen.

Besides the inhibitors which directly influence the activity of acid sphingomyelinase, the invention also includes active ingredients which influence precursors of the enzyme and/or mechanisms of activation of the enzyme. The active ingredients may also act on the formation, stabilization, mobilization and/or translocation of the intracellular vesicles in which the enzyme is located in the cell.

The invention additionally includes the use of inhibitors which influence the biological effect of the products resulting from the enzymatic reaction of acid sphingomyelinase. These products comprise in particular ceramide which forms an essential component of the membrane platforms. The invention therefore includes inhibitors which modify and, in particular, inactivate, neutralize or destroy ceramide. Particularly preferred in this connection is the enzyme ceramide glucosyltransferase which can for example by methods of molecular biology have its expression enhanced and thus have its activity enhanced and/or which can be activated by further regulators. The inhibitors may moreover prevent the ceramides cohering so that formation of platforms is impaired. In addition, the invention includes the use of inhibitors which influence the functional capacity of the previously formed ceramide-rich membrane platforms and/or prevent the formation of the membrane platforms from the outset.

Inhibitors which are suitable according to the invention are a large number of different substances, for example peptides, proteins or else inorganic substances. The invention additionally includes nucleic acids as inhibitors as long as they act when used according to the invention as inhibitors of sphingomyelinase and/or the reaction products thereof. Suitable examples thereof are antisense molecules, especially antisense oligonucleotides, or siRNA of acid sphingomyelinase.

The inhibitors advantageously employed are pharmacological active ingredients known to inhibit the enzyme acid sphingomyelinase. Particular preference is given in this connection to antidepressants, especially tricyclic and/or tetracyclic antidepressants. Tricyclic antidepressants are able for example to bring about proteolytic degradation of the enzyme, so that the enzyme can no longer be active and ceramide formation is prevented. This reduction in ceramide liberation impedes the formation of platforms within the plasma membrane, so that infection of the cell does not occur.

The antidepressants amitryptiline and imipramine have proved to be particularly advantageous. These antidepressants are therefore particularly preferred for the use according to the invention. They are known pharmacological active ingredients (generics) which display substantially no side effects. These active ingredients can be employed in conventional dosage forms for the use according to the invention, in particular orally, intravenously, intramuscularly, topically or else by inhalation. Moreover, conventional dosages are suitable for the use according to the invention. However, the effect according to the invention may also be achieved with reduced dosages.

The invention further includes the use of inhibitors derived from tricyclic and tetracyclic antidepressants, in particular from amitryptiline and/or imipramine. These derived active ingredients have substantially the same effects as the antidepressants, but may have further advantageous properties. These substances may advantageously be modified in such a way that they are more hydrophilic than the starting substances. The effect of this is that the modified substances accumulate in the brain to a smaller extent than do the substances amitryptiline and imipramine, for example. With these two substances mentioned, accumulation in the brain can be detected after a few weeks. Further advantageous properties of derived substances may be better stability and/or bioavailability.

Besides said inhibitors it is also possible and advantageous for example to use desipramine and/or FGF (fibroblast growth factor) or substances derived therefrom as inhibitors of acid sphingomyelinase.

In a further preferred embodiment of the invention, the inhibitors are antibodies, in particular neutralizing antibodies. These antibodies are able to interact very specifically with the enzyme acid sphingomyelinase or its reaction product, in particular with ceramide. The activity of the enzyme or the biological effect of the reaction product is impaired and preferably inhibited in this way. It is very suitable to employ antibodies and inhibitor for the use according to the invention, because the antibodies are on the one hand very specific, and side effects are generally avoided. Suitable antibodies for this use according to the invention are polyclonal and, because of their particular specificity, preferably monoclonal antibodies. These antibodies may vary in origin, with particular preference for humanized antibodies. Humanized antibodies mean antibodies generated for example in mice against a particular antigen. Subcloning of murine sequences into human sequences results in a hybrid molecule in which all the murine parts (apart from the variable domains) are replaced by human sequences. This means that the resulting antibody can be employed in humans with great safety.

Substances employed in a further preferred embodiment of the invention are those which influence and, in particular, impair or inhibit the formation of ceramide-rich membrane platforms. The formation of rafts which mediate an infection is impeded in this way, or pre-existing rafts are destroyed. In this embodiment of the invention, in particular β-cyclodextrin, nystatin and/or filipin or substances derived therefrom are preferred.

In the prophylaxis and/or treatment of infectious diseases it may in some circumstances be advantageous to combine together different active ingredients of the invention.

A particular advantage of the invention is that the points of attack of the active ingredients (inhibitors), that is in particular the acid sphingomyelinase and ceramide, are located on the cell surface. These targets can therefore easily be reached by the active ingredients without the need for the active ingredients to be transported into the cells. This might represent a problem, especially for larger active ingredients such as, for example, antibodies, but advantageously does not arise with the use according to the invention.

The infectious diseases which can be treated prophylactically or therapeutically with the use according to the invention are inter alia viral, parasitic and/or mycological infectious diseases. It is additionally possible to treat infectious diseases caused by protozoa. Examples of such infectious diseases are Aids, hepatitis A, rhinoviral diseases, spring-summer meningoencephalitis (SSME), rubella, influenza and/or malaria. Successful prophylactic and/or therapeutic treatment of bacterial infectious diseases is also possible with the use according to the invention. Examples of such diseases are tuberculosis and meningococcal infections or Pseudomonas aeruginosa infections especially in cystic fibrosis. The use according to the invention can additionally be employed advantageously also in the veterinary medical sector. Examples of infectious diseases which can be treated in this connection are rinderpest and/or swine fever.

The invention additionally includes the use of inhibitors of acid sphingomyelinase and/or inhibitors of products of the reaction catalyzed by this enzyme, in particular ceramide, for producing a medicament for the prophylaxis and/or treatment of infectious diseases and of disease whose course is influenced by infections. Reference is made to the above description for further features of this use according to the invention.

The invention also includes a pharmaceutical composition which comprises at least one active ingredient according to the use according to the invention, which is a substance derived from tricyclic and/or tetracyclic antidepressants, in particular from amitryptiline and/or imipramine. The invention additionally includes a pharmaceutical composition which comprises at least an effective amount of desipramine, FGF, β-cyclodextrin, nystatin and/or filipin and/or at least one substance derived therefrom. The invention further includes a pharmaceutical composition which comprises at least one antibody, in particular a neutralizing antibody, which is directed against acid sphingomyelinase. The invention moreover includes a pharmaceutical composition which comprises at least one antibody directed against ceramide, in particular a neutralizing antibody. These pharmaceutical compositions additionally include in each case at least one pharmaceutical carrier. Conventional methods can be employed to produce these pharmaceutical compositions and corresponding medicaments. Examples of suitable dosage forms are tablets, suppositories, solutions for injection or solutions for infusion.

The invention additionally includes a method for inhibiting infections of eukaryotic cells, in particular mammalian cells, which is characterized in that acid sphingomyelinase and/or products of the reaction catalyzed by this enzyme are influenced, in particular inhibited, in their activity. This method can be carried out in vivo in the intact organism or else in cultivated systems, for example in cell cultures or tissue cultures. Reference is made to the above description for further features of this method.

Finally, the invention includes the therapy of infectious diseases and/or of diseases whose course is influenced by infections, where inhibitors which influence, preferably inhibit, the enzyme acid sphingomyelinase and/or products of the reaction catalyzed by this enzyme, in particular ceramide, are administered. This therapy takes place prophylactically and/or during or after an infection has taken place. A preventive therapy can be carried out if there is a general risk of infection or, more preferably, if there is an acute risk of infection. Reference is made to the above description for further features of this therapy according to the invention.

Said features and further features of the invention are evident from the following description of examples in conjunction with the dependent claims and the figures. It is possible in this connection for the individual features each to be implemented on its own or to be implemented together in a combination of a plurality thereof.

The figures show:

DETAILED DESCRIPTION OF DRAWINGS

Examples

Figure 1:
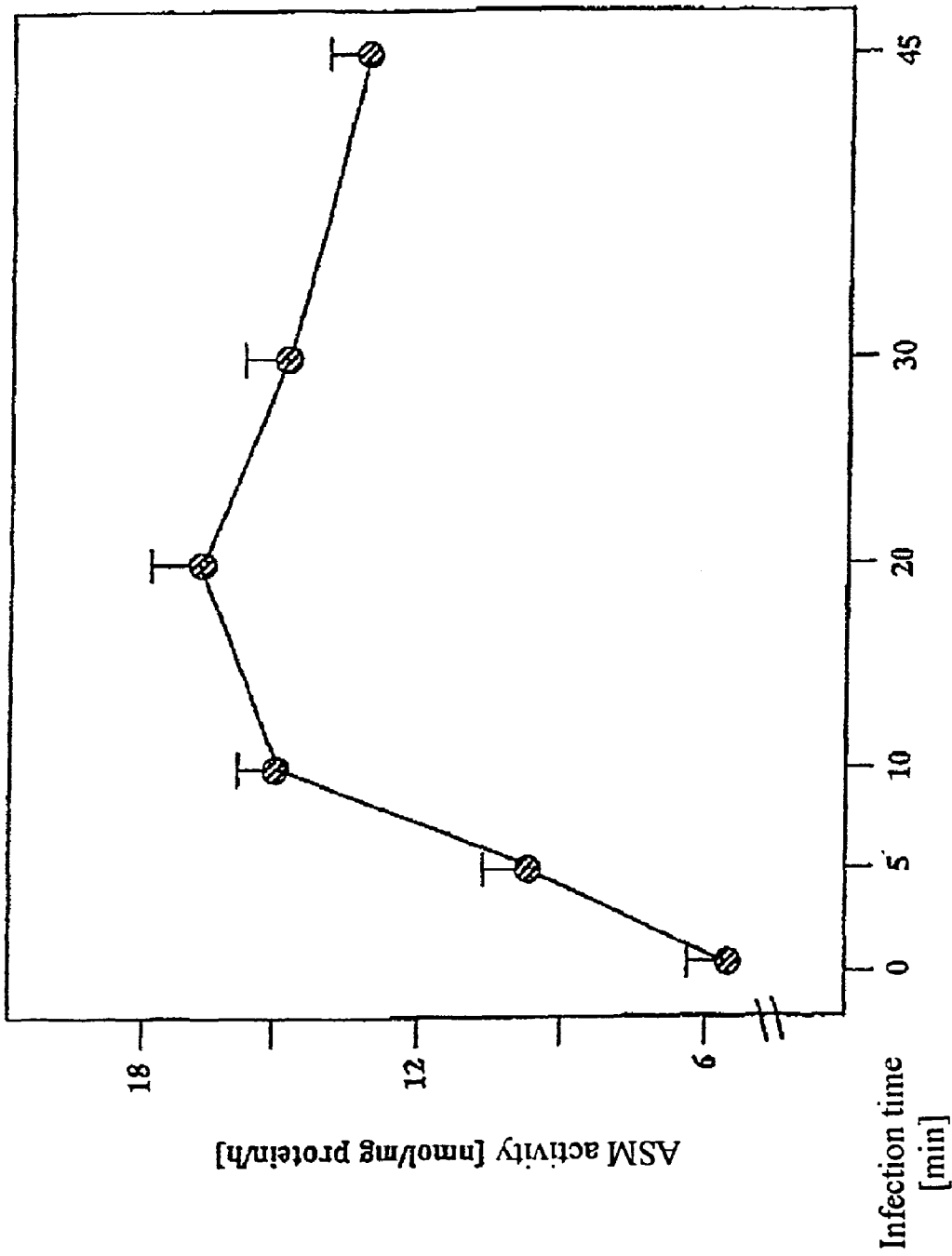
FIG. 1: Acid sphingomyelinase (ASM) is activated by infection with rhinoviruses.
Figure 2:
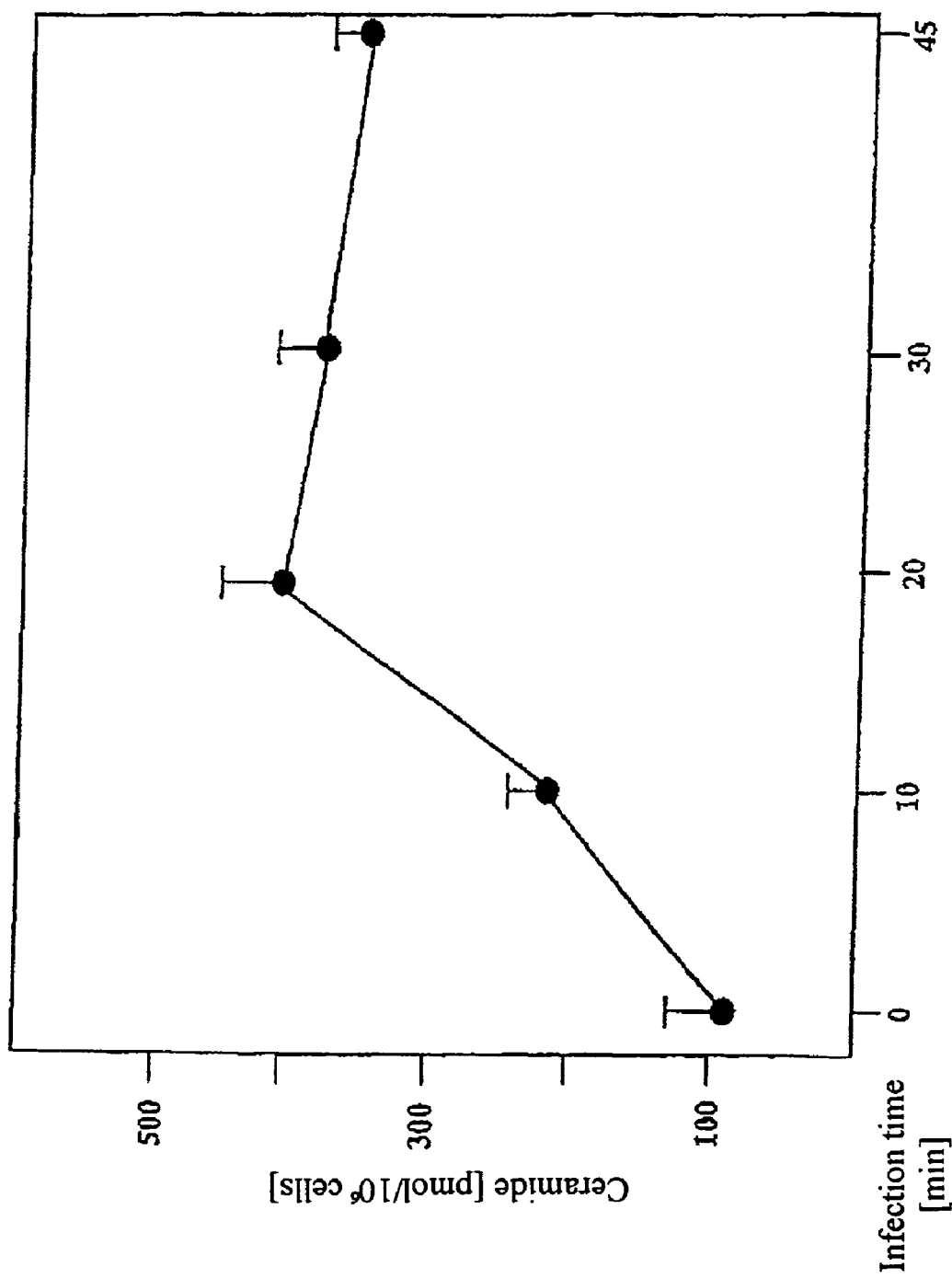
FIG. 2: Rhinoviruses induce ceramide liberation.
Figure 3:
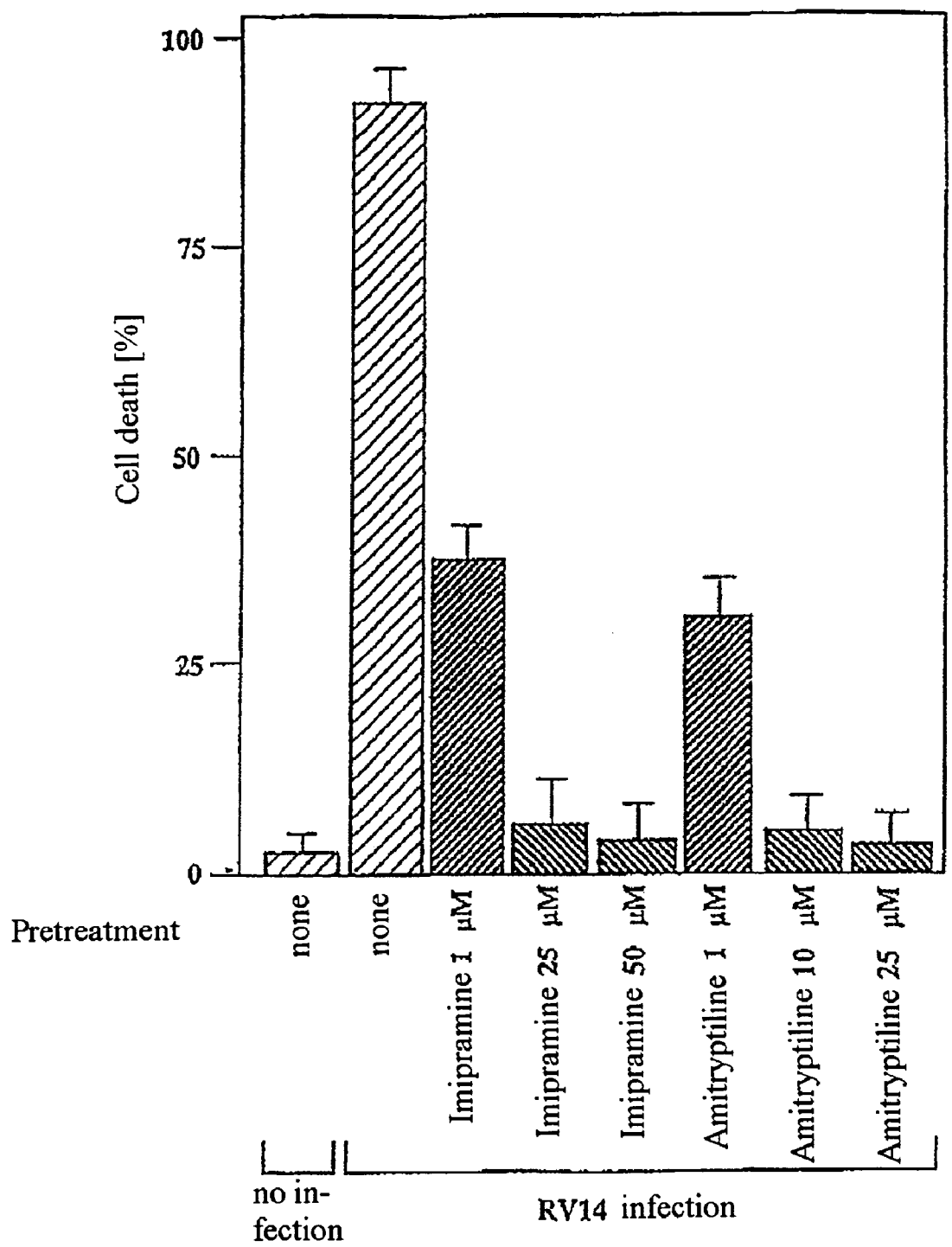
FIG. 3: Amitryptiline and imipramine inhibit dose-dependently the infection of human cells with rhinoviruses.
Figure 4:
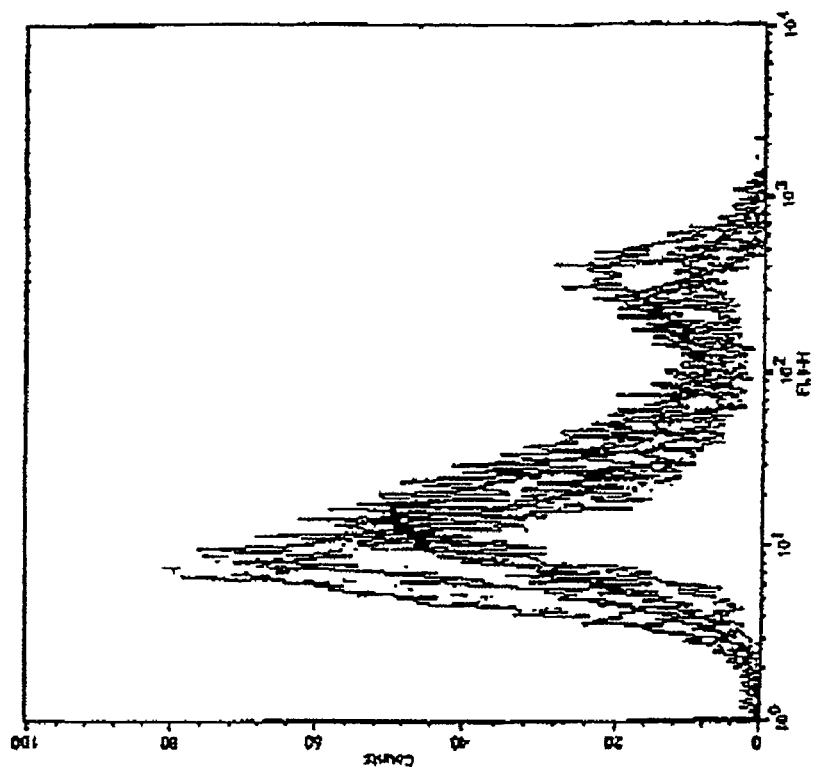
FIG. 4: The cytotoxic effect of rhinoviruses is inhibited by amitryptiline and imipramine.
Figure 4:
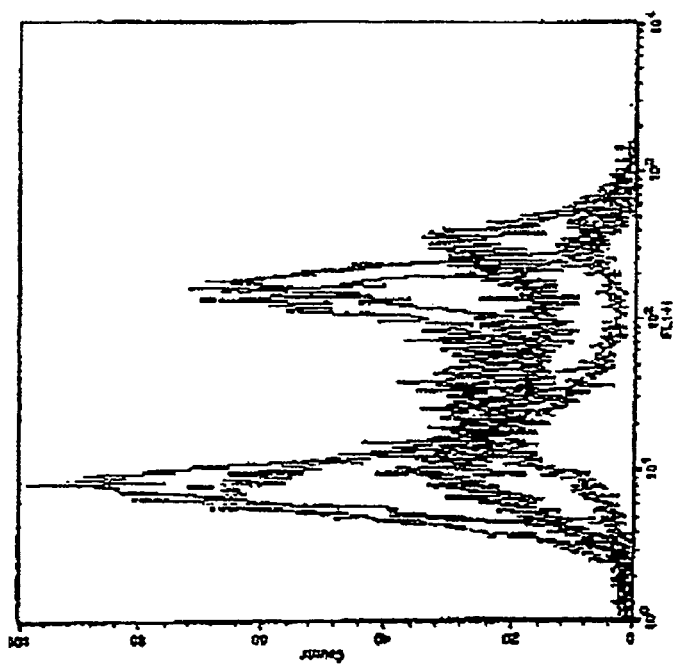

The results of the experiments with rhinoviruses show that infection of human epithelial cells with various rhinoviruses (HRV strain 14 and 16) leads to activation of acid sphingomyelinase (FIG. 1) and liberation of ceramide (FIG. 2).

a) Infection of human epithelial cells (Hela or human ex vivo epithelial cells) activates acid sphingomyelinase (ASM) three- to four-fold within 10 to 15 min. This was shown for Hela cells as example. The results are summarized in FIG. 1. The cells were infected with rhinoviruses (strain 14, MOI 25), and the sphingomyelinase activity in cell lysates was measured. For this purpose, the cells were washed after the infection, taken up in 250 mM sodium acetate (pH 5.0), 1.3 mM EDTA and 0.05% NP40, disrupted by ultrasound treatment with a sonicator probe at low energy, and incubated with [$^{14}$C]sphingomyelin (0.5 μCi/sample, 54.5 mCi/mmol; NEN) for 30 min The in vitro enzyme assay was stopped by adding 800 μl of a 2:1 column mixture of $CHCl_3$ and $CH_3OH$ (v/v) and 200 μl of $H_2O$, and the liberation of [$^{14}$C]phosphorylcholine into the aqueous supernatant was measured by scintigraphy after organic extraction. Means±standard deviation for three experiments are shown. Preincubation of the cells with an inhibitor of acid sphingomyelinase, i.e. amitryptiline, blocks the activity of acid sphingomyelinase.

b) The stimulation of acid sphingomyelinase correlates with a liberation of ceramide from the infected cells. This is depicted in FIG. 2. The infection of human epithelial cells (Hela) leads to liberation of ceramide within a few minutes after infection. Hela cells were again infected with rhinoviruses (strain 14) for this purpose. Ceramide was measured by a diacylglycerol (DAG) kinase assay (Grassme et al., Cell 91, 605-615, 1997). Ceramide was converted into [$^{32}$P]-ceramide by adding DAG kinase and [$^{32}$P]γATP. The phosphorylated ceramide was fractionated by thin layer chromatography and determined by scintigraphy. Means±standard deviation of three experiments are depicted. Preincubation of the cells with amitrytiline abolishes the liberation of ceramide.

c) Infection of human epithelial cells with rhinoviruses induces the formation of ceramide-rich membrane platforms. Both acid sphingomyelinase and ceramide are to be found on the surface in membrane platforms to which the rhinoviruses also bind after an infection. As experimental demonstration thereof, human nasal epithelial cells were infected with rhinovirus strain 14 for 20 min, fixed and stained with Cy3-labeled monoclonal anti-ceramide antibodies (Alexis). Under the confocal microscope, the formation of a ceramide-rich membrane platform was evident a short time after the infection. Uninfected cells showed no ceramide on the cell surface.

d) Pharmacological inhibition of acid sphingomyelinase blocks infection of human epithelial cells by rhinoviruses dose-dependently up to almost complete inhibition of infection. The drugs used were the drugs (antidepressants) imipramine and amitryptiline, which block up to 98% of acid sphingomyelinase activity within 20 min in control experiments. Infection of human epithelial cells by rhinoviruses was measured in flow cytometric analyses of the cytopathic effect of the viruses. Since rhinoviruses induce cell death in these cells, it is possible to use cell death as a measure of infection of the cells. The dose-effect plot for the inhibition of infection of human epithelial cells by imipramine and amitryptiline is depicted in FIG. 3. For this, human Hela epithelial cells were infected with the rhinovirus strain 14 for 24 h, and the cytotoxic effect of the viruses was measured by flow cytometry after staining with FITC-annexin. Amitryptiline and imipramine, which inhibit acid sphingomyelinase, were added to the cells in a serum-free medium 30 min before infection of the rhinoviruses. The data show that the drug almost completely inhibits the viral infection. Amitryptiline and imipramine themselves had no cytotoxic effect on the cells. The means±standard deviation of three experiments are shown.

e) The cytotoxic effect of rhinoviruses is inhibited by amitryptiline and imipramine. FIG. 4 shows the representative flow cytometric analysis of the inhibition of infection of Hela cells by rhinoviruses after treatment with amitryptiline. For this, human Hela epithelial cells were infected with various rhinovirus strains (RV14, RV16) for 24 h. The infection was measured by means of the cytotoxic effect of the viruses and was determined by staining the cells with FITC-annexin in a flow cytometer. A shift of the plot to the right means an increase in the FITC-annexin binding and is thus a measure of cell death. Amitryptiline and imipramine were added as inhibitors of acid sphingomyelinase to the cells in a serum-free medium 30 min before infection with the rhinoviruses. The data show that the drugs almost completely inhibit the viral infection. The effect of amitryptiline is shown, and analogous data were obtained for imipramine. The depiction on the left in FIG. 4 shows the effect without addition of active ingredient, and the depiction on the right shows the effect with addition of active ingredient.

f) Therapy of Hela cells with anti-ceramide antibodies almost completely inhibits infection of the cells with rhinoviruses. For corresponding experiments, anti-ceramide antibodies (from Alexis) were added in a concentration of 5 ng/ml to the cells with the viruses (rhinovirus strains 2, 14 and 16). There was approximately 95% inhibition of infection of the cells with the rhinoviruses.

2. Infection with HIV

HIV infects human cells essentially through binding of the gp120 molecule of the virus to the CD4 there is only inefficient infection of cells with HIV. The gp120 molecule forms with the gp41 molecule an oligomeric complex in which gp120 to the CD4 molecule on T lymphocytes alters the confirmation of gp120; in particular there is a change in the conformation of the variable loop, thus exposing the so-called corecptor binding site. Via this binding site, gp120 binds to a coreceptor, usually the cytokine receptors CCR5 or CXCR4. In total, more than 14 different coreceptors have been identified, but only CCR5 or CXCR4 appear to be of great in vivo importance. Uptake of the virus into the cell is initiated through the binding of HIV to CD4 and further coreceptors (Clapham P. R., McKinght A. (2001). HIV-1 receptors and cell tropism. British Medical Bulletin 58: 43-59)

The CD4 molecule is constitutively present, i.e. also in uninfected cells, in rafts. Infection with HIV is followed by redistribution of CD4 and concentration of CD4 in a relatively small region of the plasma membrane (Popik W., Alce T. M., Au W. C. (2002). Human Immunodeficiency Virus Type 1 uses lipid raft-colocalized CD4 and chemokine receptors for productive entry into CD4+T cells. J. of Virology 76: 4709-4722). This phenomenon of a local, very large accumulation of a molecule is referred to as clustering or aggregation. CD4 colocalizes after infection in these clusteres with GM1, a typical marker of rafts, and also CCR5 and CXCR4, which are recruited after stimulation into the newly formed membrane platforms. If rafts are destroyed by preincubation of the cells with reagents which extract cholesterol, in these studies both the aggregation of CD4 after infection and the infection of the T cells themselves was prevented. Binding of the virus to CD4 was unchanged, by contrast. This shows that membrane rafts play an outstanding part in the infection of human cells with HIV. The mechanisms which serve for fusion of many small rafts to large membrane platforms, and those which serve for aggregation of CD4 and the recruitment of coreceptors, and eventually appear to mediate the infection, are as yet unknown, however.

Figure 5:
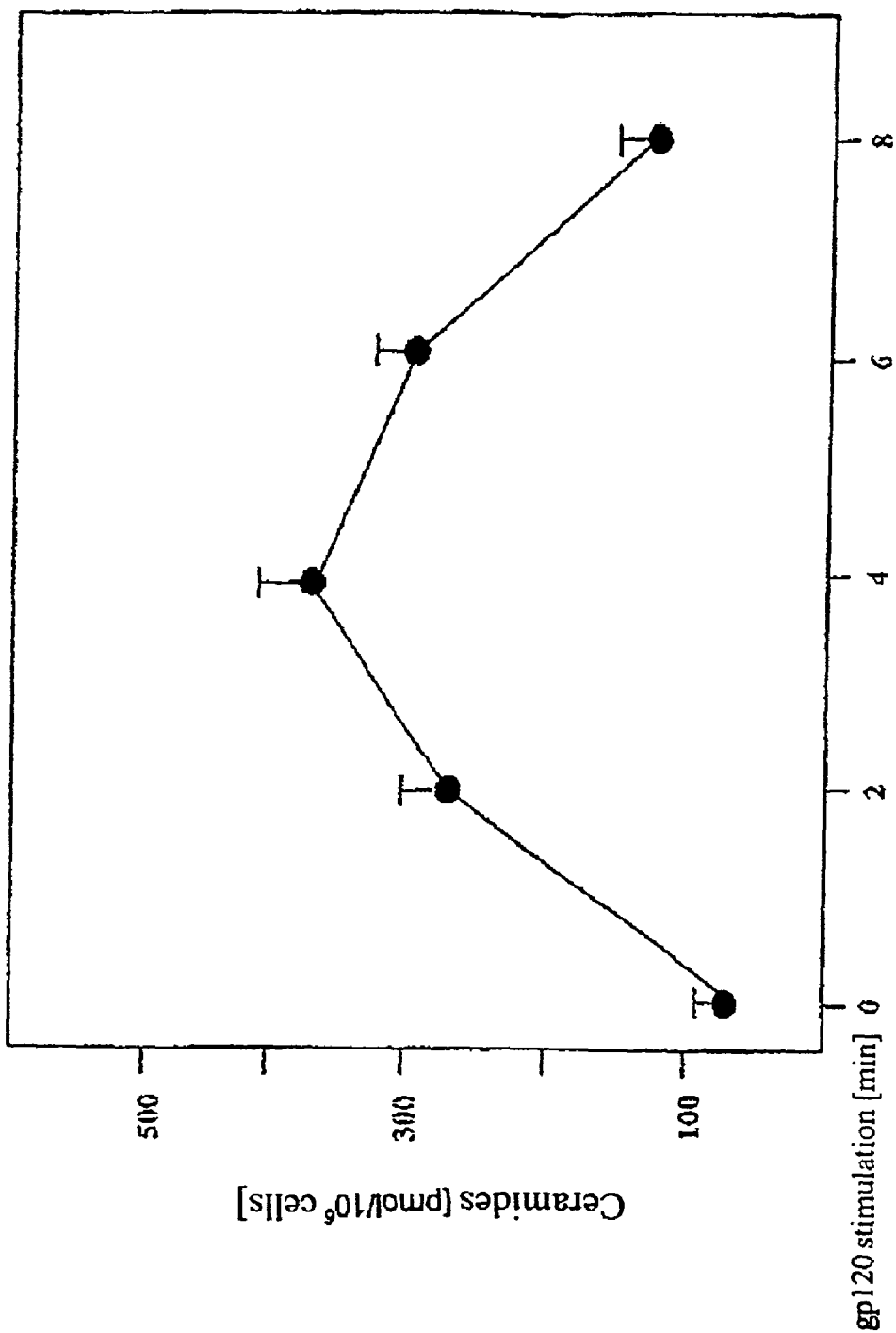
FIG. 5: HIV gp120 induces the liberation of ceramide in human T lymphocytes.
Figure 6:
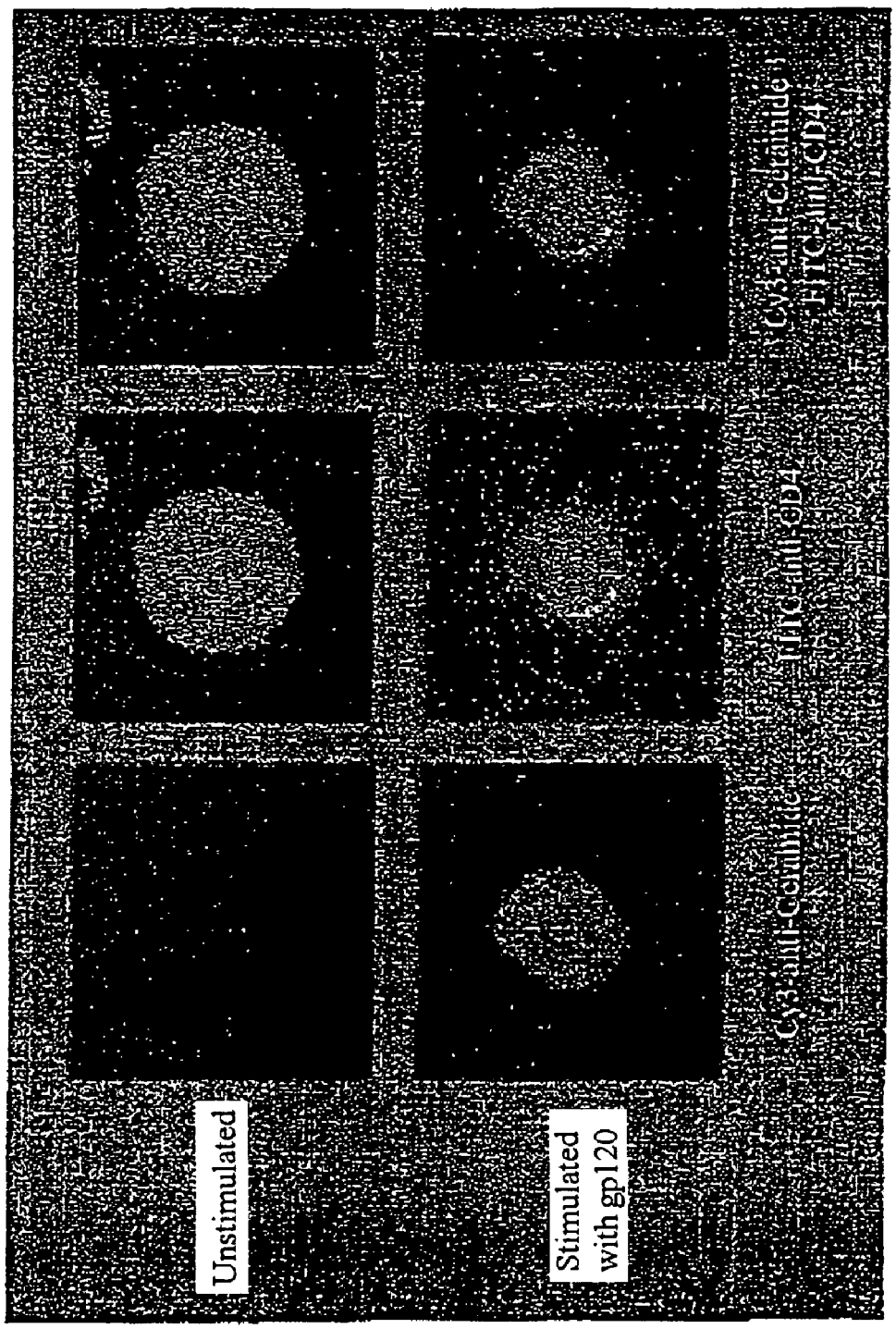
FIG. 6 Cellular stimulation with gp120 induces ceramide-rich membrane platforms.

The following results show by means of a stimulation of human T lymphocytes with recombinant gp120 that HIV makes use of ceramide-rich membrane platforms in order to infect human cells.

a) Within a few minutes, gp120 induces the liberation of ceramide in human T lymphocytes. FIG. 5 shows the therapy of human CD4-positive lymphocytes with 10 μg/ml recombinant gp120. Ceramide is liberated within 1 minute. Ceramide was determined using a DAG kinase assay.

b) Liberation of ceramide from human T lymphocytes after stimulation with gp120 correlates with the formation of ceramide-rich membrane platforms in the plasma membrane of stimulated cells, in which the CD4 molecule colocalizes and forms clusters. FIG. 6 shows that cellular stimulation with gp 120 induces ceramide-rich membrane platforms. Stimulation of human CD4-positive T cells with gp120 (10 μg/ml) leads to the formation of ceramide-rich membrane platforms within 2 minutes. The formation of ceramide-rich membrane domains was determined by fluorescent microscopy after labelling the cells with a Cy3-labeled anti-ceramide antibody. CD4, which was visualized with an FITC-labeled antibody, aggregates in these ceramide-rich membrane platforms.

Quantitative analyses of the formation of ceramide-rich membrane platforms show that 50±7% of all CD4-positive T lymphocytes have a ceramide-rich membrane platform 5 min after stimulation.

3. Infection with *Pseudomonas aeruginosa*

The importance of ceramide-rich membrane platforms for infections with pathogenic bacteria and viruses was shown for the example of infection of mammalian cells with Pseudomonas aeruginosa. Activation of acid sphingomyelinase and liberation of ceramide were observed after infection with *aeruginosa* both in vitro after infection of Chang epithelial cells, WI-38 fibroblasts, ex vivo lung fibroblasts, ex vivo cultivated tracheal epithelial cells and in vivo in tracheal epithelial cells. Liberation of ceramide after infection takes place in rafts which are reorganized by the liberated ceramide to large membrane platforms. The liberated ceramide and the acid sphingomyelinase are localized in the newly formed membrane platforms after infection with *P. aeruginosa*.

The importance of acid sphingomyelinase for the formation of membrane platforms after *P. aeruginosa* infection is shown by the complete absence of ceramide-rich membrane platforms after infection of cells deficient in acid sphingomyelinase. The roe of ceramide-rich membrane platforms for infection with *P. aeruginosa* was investigated in cells deficient in acid sphingomyelinase, and by destroying rafts with drugs which interfere with cholesterol metabolism. These drugs are β-cyclodextrin, nystatin and filipin. Removal of cholesterol from membrane rafts leads to a collapse of rafts. In vivo, rafts in the lung were destroyed by pulmonary lavage with β-cyclodextrin, nystatin and filipin, or normal mice and mice deficient in acid sphingomyelinase were used. The results show that ceramide-rich membrane platforms regulate the internalization of bacteria into epithelial cells, the death of infected cells and the release of proinflammatory cytokines.

The in vivo importance of these finding was shown in infection experiments with normal mice and mice deficient in acid sphingomyelinase. Whereas normal mice recover from pulmonary infection with *P. aeruginosa* within a few days, the mice deficient in acid sphingomyelinase were very sensitive to pulmonary *P. aeruginosa* infection and died of sepsis within a few days after the start of infection.

The invention claimed is:

1. A method of treating cystic fibrosis, comprising:
   administering to a patient by inhalation, a formulation consisting essentially of a carrier and an antidepressant selected from the group consisting of a tricyclic antidepressant, and a tetracyclic antidepressant.

2. The method of claim 1, wherein the antidepressant is a tricyclic antidepressant.

3. The method of claim 1, wherein the antidepressant is a tetracyclic antidepressant.

4. The method of claim 1, wherein the antidepressant is selected from the group consisting of amitryptiline and imipramine.

5. The method of claim 1, wherein the antidepressant is amitryptiline.

6. The method of claim 1, wherein the antidepressant is imipramine.

* * * * *